United States Patent [19]
Li et al.

[11] Patent Number: 5,612,049
[45] Date of Patent: Mar. 18, 1997

[54] BIOACTIVE COATINGS AND THEIR PREPARATION AND USE

[75] Inventors: Panjian Li, Oegstgeest, Netherlands; Ilkka Kangasniemi, Turku, Finland

[73] Assignee: Axidental Oy, Turku, Finland

[21] Appl. No.: 302,884

[22] PCT Filed: Apr. 21, 1993

[86] PCT No.: PCT/FI93/00163

§ 371 Date: Dec. 7, 1994

§ 102(e) Date: Dec. 7, 1994

[87] PCT Pub. No.: WO93/21969

PCT Pub. Date: Nov. 11, 1993

[30] Foreign Application Priority Data

Apr. 23, 1992 [FI] Finland .................................. 921802

[51] Int. Cl.$^6$ .................................................. A61F 13/00
[52] U.S. Cl. ............................. 424/422; 424/9.3; 424/9.4
[58] Field of Search ........................... 424/9.3, 9.4, 422; 623/16; 428/403; 501/95

[56] References Cited

U.S. PATENT DOCUMENTS

| | | | |
|---|---|---|---|
| 4,737,411 | 4/1988 | Graves et al. | 428/403 |
| 5,032,552 | 7/1991 | Nonami et al. | 501/95 |
| 5,045,318 | 9/1991 | Tengvall et al. | 424/422 |
| 5,152,993 | 10/1992 | Bjursten et al. | 424/422 |
| 5,211,661 | 5/1993 | Shinjou et al. | 623/16 |

FOREIGN PATENT DOCUMENTS

0409810A2  1/1991  European Pat. Off. .

*Primary Examiner*—Thurman K. Page
*Assistant Examiner*—William E. Benston, Jr.
*Attorney, Agent, or Firm*—Ronald J. Kubovcik

[57] ABSTRACT

Novel coating materials for biomedical applications, particularly for use on biomedical implants, the coating material containing gel-derived titania where the material is capable of inducing calcium phosphate formation onto its surface under in vitro conditions, e.g. in a simulated body fluid and/or under in vivo conditions, processes for the preparation of the coating materials as well as their use in biomedical implant technology.

16 Claims, 4 Drawing Sheets

BIOACTIVE COATINGS AND THEIR PREPARATION AND USE

This invention relates to novel bone-bonding gel-derived titania-based coatings. The invention also includes processes for the preparation of such coatings and their uses as surgical implants.

Titanium and its alloys are extensively used in reconstruction surgery as dental and orthopaedic implants because of their excellent biocompatibility with bone tissue (P. I. Brånemark, J. Prosthetic Dent. 50:399–410, 1983; D. I. Bardos, D. Williams (ed), Concise Encyclopedia of Medical & Dental Materials, Pergamon Press, Oxford 1990, pp 360–365; R. van Noort, J. Mater. Sci. 22:3801–3811, 1987). This can be explained by the unique characteristics of titanium-bone interface. The extremely slow growth of titanium oxide was observed during the implantation. The TiOH groups within the hydrated oxide layer were considered to be involved in the events leading to osseointegration of the titanium implants (P. Tengwall & I. Lundström, Clinical Materials 9:115–134, 1992). The calcium and phosphorous groups were identified in the few nanometer thick oxide layer (D. Mcqueen et al, Clinical application of Biomaterials, John Wiley & Sons, Chichester, 1982, pp. 167–177). Although titanium implants could be fixed in bone bed through osseointegration by using appropriate surgical techniques, the fixation proceeds slowly and depends largely on surgery (L. Sennerby, PhD thesis, University of Gotenburg, Gotenburg, Sweden, 1991). To enhance the bonding process and improve the bonding strength, the plasma-sprayed coatings of apatite, more particularly hydroxyapatite, were developed and approved for clinical application (K. de Groot, J. Ceram. Soc. Japan 99:943–953, 1991). However, from a technical point of view, plasma spraying is cumbersome and essentially complex, because apatite powder is chemically unstable at elevated temperatures.

Implants can chemically bond to bone through apatite because bone mineral is hydroxyapatite. These bone-bonding implants could be wholly apatite ceramic or coated with apatite using specific techniques such as plasma spray coating process. Furthermore, apatite can also be used as a bioactive phase in some composites to make them bond to bone (K. Verheyen, Resorbable materials with bone bonding ability, PhD thesis, Leiden University, Holland, 1993). In contrast to those apatite-based materials, bioactive glasses and glass-ceramics develop apatite layer onto their surfaces after implantation within bone tissue (L. L. Hench, Bioceramics: from concept to clinics, J. Am. Ceram. Soc. 74:1487–510, 1991; T. Kokubo, Bioactive glass ceramics: properties and application, Biomaterials 12:155–163, 1991). This kind of apatite gives the glasses and glass-ceramics a bone-bonding strength stronger than apatite ceramics (T. Kokubo, Bioactivity of glasses and glass-ceramics, in Bone-bonding Biomaterials, P. Ducheyne, T. Kokubo and C. A. van Blitterswijk (eds), Reed Health-care Communication, Holland, 1992, pp. 31–46). This bone-like apatite formation results from the interaction of these bioactive glasses and glass-ceramics with the surrounding biological tissue and especially with body fluid.

The potential for apatite formation can be evaluated for materials by using a metastable calcium phosphate solution, called a simulated body fluid (SBF, $Na^+$ 142, $K^{30}$ 5.0, $Mg^{2+}$ 1.5, $CA^{2+}$ 2.5, $Cl^-$ 148, $HCO_3^-$ 4.2, $HPO_4^{2-}$ 1.0 and $SO_4^{2-}$ 0.5 in mM). The fluid has been used in in vitro studies to provide information about the process of bone-like apatite formation on these bioactive glasses and glass ceramics because of its ion concentrations nearly equal to those of human blood plasma (T. Kokubo et al, J. Biomed. Mater. Res. 24, 721–734, 1990). Moreover, it does help a great deal to assess the possibility of bone-bonding for materials before their in vivo study. Those materials which can induce apatite formation on their surfaces in SBF can be placed in the list of candidates for bone-bonding materials. Recent research showed that besides bioactive glass and glass-ceramics, also pure silica prepared by sol-gel method can successfully induce bone-like apatite formation on its surface whereas pure silica glass and quartz both synthesized at high temperature cannot (P. Li et al "Apatite formation induced by silica gel in a simulated body fluid", J. Am. Ceram. Soc. 75: 2094–2097, 1992). One difference in characteristics among these three silica exists in the density of silanol groups (SiOH). The gel-derived silica has abundant SiOH groups whereas both silica glass and quartz do not have. Furthermore, bioactive glasses prepared by sol-gel process were reported to form apatite faster than the same glasses but prepared through conventional melting methods (R. Li et al, J. App. Biomater. 2:231–239, 1991).

Based on these findings, we suspected that titania is also an apatite inducer if it is prepared by sol-gel method. In vitro study with the titania gel showed evidence to support our speculation. It was found that apatite is induced by the titania gel when soaked in SBF both as bulk and as coating. FIG. 1(A) represents a scanning electron microscopic (SEM) micrograph showing a) hydroxyapatite formation on the bulk after it is soaked in SBF, while FIG. 1(B) is an SEM micrograph of gel-derived titania coating after it is soaked in SBF. The implantation with gel-derived titania coated titanium plugs in the femura of goats revealed that calcium phosphate could accumulate and deposit onto and/or within the titania gel coating. As shown in FIG. 2, this calcium phosphate layer bridges the bone and the coating so that they can bond to each other. We consider that abundant TiOH groups contained in gel-derived titania are responsible for its high affinity for calcium and phosphate.

Swedish Patent No. 464911 describes a Ti-gel film produced by treating the titanium surface with hydrogen peroxide under certain conditions. The reaction was considered to alter $TiO_2$ into $TiO_{4-x}(OH)x$. The patent claimed such a surface to possess anti-inflammatory properties. The inventors suggested that "such a gel-surface resulting from the reactions in vivo might have something to do with a formation of chemical bonding of the bone to the titanium implants". However, the document did not show any evidence or indication that the treated titanium surface might be bioactive. There is no mention of a Ca, P-layer, which is generally accepted as a prerequisite for the bone bonding to occur. Our experiments clearly demonstrated that a Ca, P-layer forms onto the titania-gel derived coating both in vitro and in vivo, which is a basic difference from the Ti-gel surface described in the Swedish patent.

The apatite induction capacity of gel-derived titania could be enhanced by the corporation of, for instance, CaO, $P_2O_5$, $Na_2O$ or $SiO_2$ into the titania. They can be introduced during the process to make titania-based materials. As a matter of fact, the effect of these additive compounds on bone-bonding has been determined for bioactive glasses and glass-ceramics (L. L. Hench: "The compositional dependence of bioactive glasses and glass ceramics", P Vincenzine (ed), Ceramics in substitutive and reconstructive surgery, Amsterdam, Elsevier, 1991, pp. 259–274). $Al_2O_3$, $B_2O_3$, $MgO$ and $K_2O$ may be added as well. They can remain in the oxide form within the coating or, at least to some extent, release the corresponding ions.

In addition to the sol-gel process used for the preparation of titania having sufficient TiOH groups, a galvanic process can also be considered. Our studies have shown that the gel-like surface formed on a negative titanium pole when two pieces of titanium plates were placed at a distance in a hydroxide solution ($Ca(OH)_2$ in this case) with a proper Ph value under certain voltage. FIG. 3 shows SEM photograph of Ti-gel formed on the negative Ti-pole where SEM-EDX showed the accumulation of Ca and P when soaked in SBF (original magnification: 680×, bar (white) 100 μm).

This gel was thus capable of attracting Ca and P ions from surrounding calcium phosphate solution. Such surface could be expected to promote bone-bonding compared to untreated titanium surfaces. Oxides of Ca, P, Na, Si, Al, B, Mg and K may also be added during the galvanic process to improve the coatings.

It can be expected that a strong bonding between titanium implant and gel-derived titania-based coating can be developed through a passivating titanium oxide layer which could secure a lasting strong bone bonding. Furthermore, it is simple in technique to develop the gel-derived titania coating on titanium and its alloys compared with plasma-sprayed technique. Hence, the development of gel-derived titania-based coatings on titanium and its alloys is highly interesting from both scientific and application points of view. Such gel-derived titania-based materials are believed to give rise to an entirely new generation of bone-bonding materials.

Thus, one object of the invention is a novel gel-derived titania-based coating material having abundant TiOH groups for biomedical application, said coating material being capable of inducing apatite formation onto its surface under in vitro conditions, e.g. in a simulated body fluid, and/or calcium phosphate deposition under in vivo conditions. According to one aspect of the invention, the coating material can further comprise one or more of the following elements either as ions or as oxides: Ca, P, Si, Na, K, B, Mg and Al. These additives are introduced to enhance calcium phosphate formation and improve the stability of the coating.

Another object of the invention is a method for the preparation of a gel-derived titania-based coating material according to a sol-gel method.

Another object of the invention is a method for the preparation of a gel-derived titania-based coating material by a galvanic process. Preferably the process is carried out in a hydroxide solution where titanium is used as the positive as well as the negative pole. According to this process a titania gel surface is formed on the negative pole.

Another object of the invention is a method for the preparation of a gel-derived titania-based coating material according to a sol-gel method or the galvanic method wherein one or more of the following oxides are added to the process: $CaO$, $P_2O_5$, $Na_2O$, $SiO_2$, $K_2O$, $Al_2O_3$, $B_2O_3$ and $MgO$.

A further object of the invention is an implant for biomedical application comprising of a substrate and a gel derived titania-based coating material thereon, said coating material being capable of inducing apatite formation onto its surface under in vitro conditions, e.g. in a simulated body fluid, and/or calcium phosphate deposition under in vivo conditions.

According to one aspect of the invention the substrates are tooth, hip or other Joint implant substrates, or other biomedical implant substrates.

According to another aspect of the invention the substrate is a polymeric, metallic, ceramic, carbon substrate or a composite substrate comprising one or more of said components.

According to a preferred aspect of the invention the substrate is titanium or a titanium alloy.

A further object of the invention is an implant for biomedical application comprising of a substrate and a gel-derived titania-based coating material thereon, said coating material being capable of inducing calcium phosphate formation onto its surface in vitro e.g. in a simulated body fluid and/or in vivo, wherein the coating material further comprises one or more of the following elements either as ions or as oxides: Ca, P, Si, Na, K, B, Mg or Al.

According to a further aspect of the invention the implant comprises a substrate and an apatite layer, said layer having been grown on a gel-derived titania coating in a synthetic solution, preferably a SBF solution.

According to a further aspect of the invention the implant comprises a substrate and a layer being essentially a mixture of gel-derived titania and apatite, said apatite component having been grown on a gel-derived titania coating in a synthetic solution, preferably a SBF solution.

BRIEF DESCRIPTION OF THE DRAWINGS

FIG. 1(A) represents a scanning electron microscopic micrograph showing hydroxyapatite formation on bulk titania gel after it has been soaked in simulated body fluid (SBF), while

FIG. 4(A) is an SEM photograph of the surface of silica gel soaked in SBF for two weeks, while

According to the sol-gel method, a titania gel coating was prepared by a dipping process. A substrate is dipped in a ready-to-use titania sol solution and withdrew at the speed of about 5–50 cm/min. After kept at ambient temperature for 5–10 minutes, the gel film on the substrate was treated at 350°–750° C. for 3–30 minutes and then allowed out the oven to cool in air. Subsequently, the coating was given a ultrasonic cleaning in: (a) acetone for 3–10 minutes; (b) ethanol for 3–10 minutes. After that, the coating was rinsed with deionized water and dried. The devices can be repeatedly coated for several time to obtain thicker titania gel coatings. The titania sol solution was prepared by hydrolyzation of tetraisopropyl orthotitanate ($Ti(C_3H_7O)_4$). 5–20 grams of this titanium alkoxide was dissolved into 10–30 grams of absolute ethanol. The hydrolyzation of titanium alkoxide takes place when the above solution is mixed at 0° C. with another ready-to-use solution with the composition: absolute ethanol 5–15, ethylenglycolmonoethylether ($C_4H_{10}O_2$) 2–5, $H_2O$ 0.5–1.5 and condensed HCl 0.5–1.5 in gram. The titania sol solution is then used for coating after its aging for 0.5–30 hours. A bulk titania gel was prepared by evaporating HCl-peptized amorphous titania sol 50 nm in size in an oven at 80° C. The gel was heated at 400°–780° C. for 2 hours. A silica gel was prepared by hydrolysis of tetrahydroxysilane in an aqueous solution containing polyethylene glycol with average molecular weight of 10,000 and small amount of nitric acid. The organic phase was leached out in ethanol-water solution. The gel was heated at 400° C. for 2 hours. An alumina gel was prepared by evaporating HCl-peptized amorphous alumina sol 100×10 nm in size in an oven at 80° C. The gel was heated at 450° C. for 2 hours.

A rectangular piece 6×6×1.5 mm$^3$ of the gels was soaked in 12 ml of SBF. The concentrations of Ca and P in the fluid were monitored with inductively coupled plasma (ICP) emission spectroscopy during the soaking. After various periods, the gel pieces were removed from the fluid and their surfaces were analyzed with a thin-film X-ray diffraction (TF-XRD), Fourier transform infra-red reflection spectroscopy (IRRS) and scanning electron microscopy (SEM).

Figure 1A:
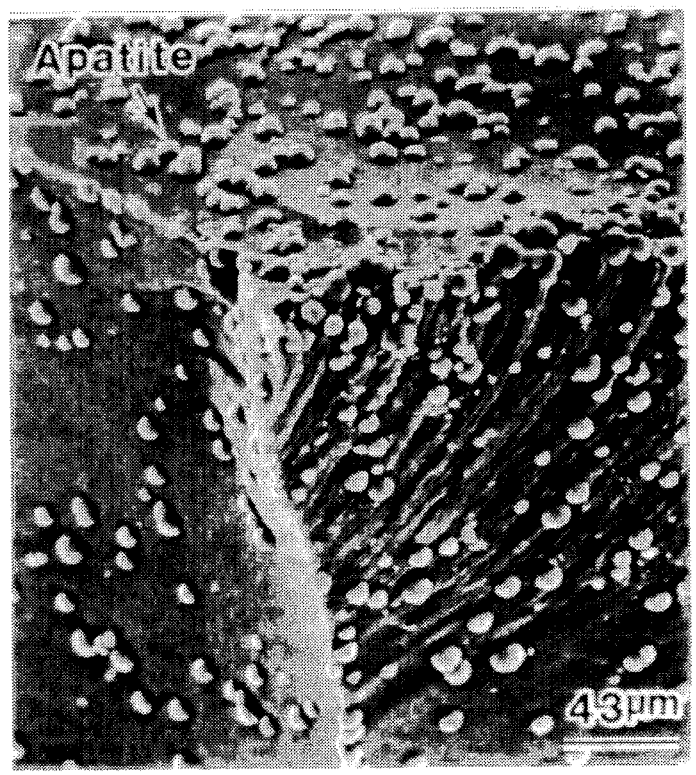
Figure 1B:
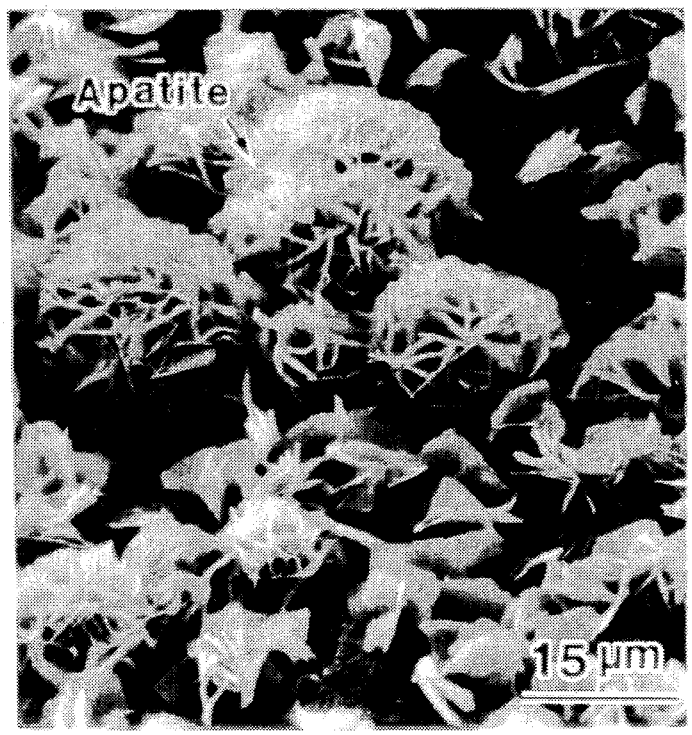
FIG. 1(B) represents a scanning electron microscopic micrograph showing a coating of gel-derived titania after soaking in SBF.
Figure 2:
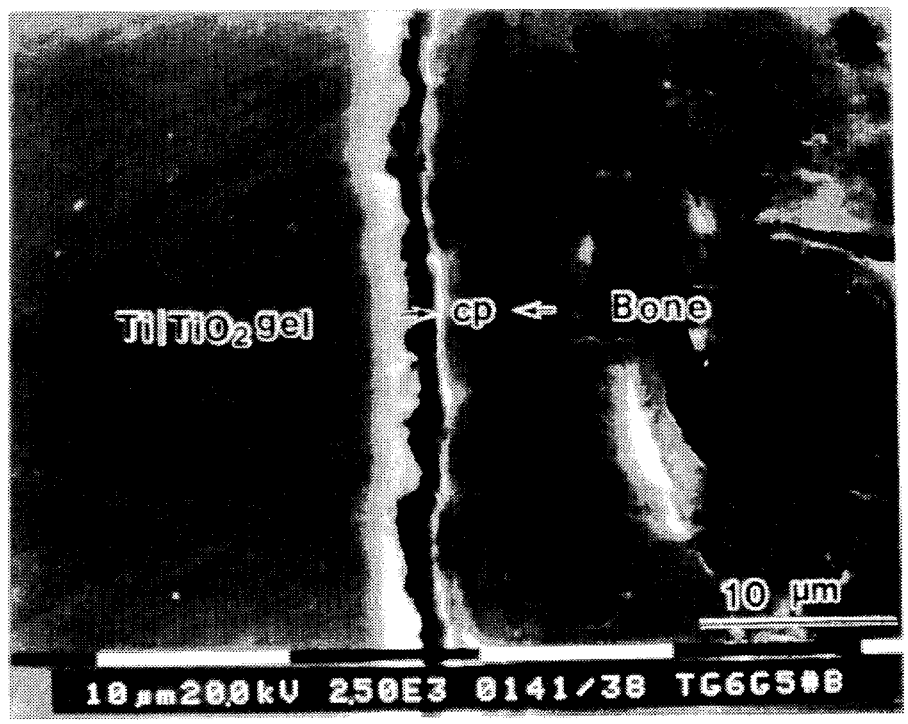
FIG. 2 illustrates a scanning electron microscopic micrograph of a calcium phosphate layer bridging a bone and a titania gel coating.
Figure 3:
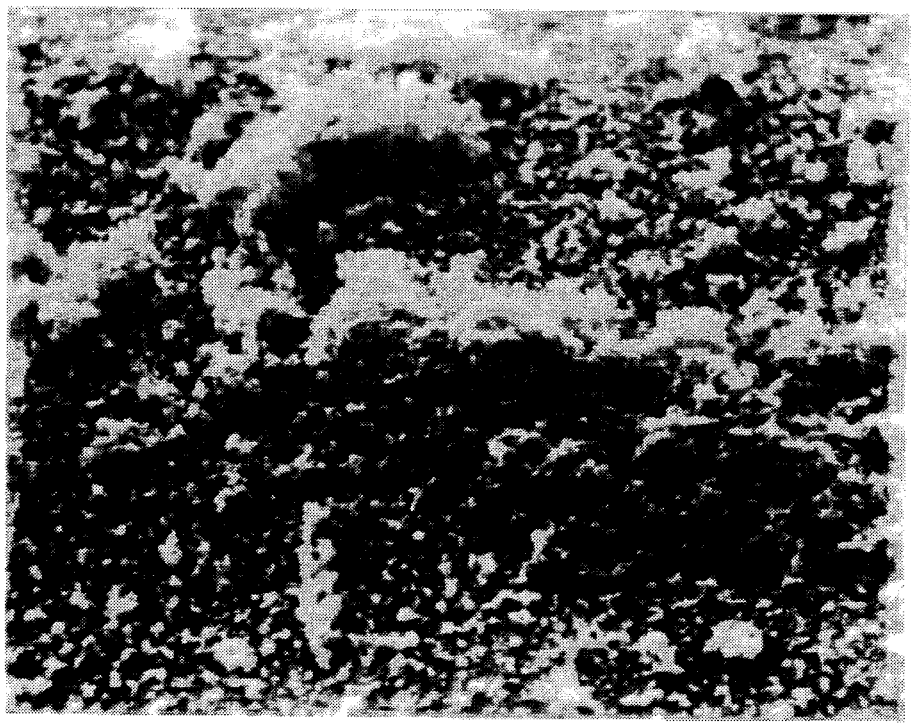
FIG. 3 shows an SEM photograph of Ti-gel formed on the negative Ti-pole where SEM-EDX showed the accumulation of Ca and P when soaked in SBF (original magnification: 680×, bar (white) 100 μm).
Figure 4A:
Figure 4B:
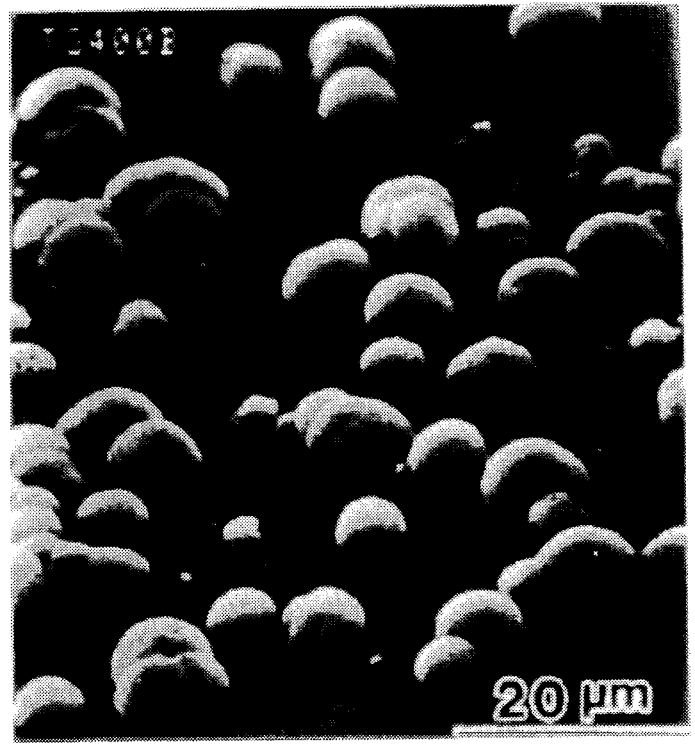
FIG. 4(B) is an SEM photograph of the surface of titania gel soaked in SBF for two weeks.

ICP measurements showed that Ca and P concentrations in the fluid appreciably decreased with soaking of the titania and silica gel. Soaking of alumina gel did not affect the Ca and P concentration. FIG. 4(A) shows a SEM photograph of the surface of the silica gel soaked in SBF for 2 weeks; FIG. 4(B) shows titania gel soaked in SBF for 2 weeks. It can be seen from FIGS. 4(A) and 4(B) that a certain kind of deposition is formed on the surfaces of both silica and titania gel. No deposition was observed on an alumina gel. The deposit on the silica and titania gels was identified as a carbonate-containing hydroxyapatite of small crystallites and/or defective structure, similar to the apatite in the natural bone, by the TF-XRD and IRRS. It is apparent from the results that both gel-derived silica and gel-derived titania induces apatite formation.

A model is produced to explain the apatite induction from physiological-related fluids. It is considered that both silica gel and titania gel are capable of inducing apatite formation due to their abundant OH groups and negatively charged surfaces at physiological pH 7.4. The surfaces with negative charge has high affinity for Ca ions which can be accumulated around the surfaces because of Coulomb's force. Meanwhile, phosphate groups are attracted by abundant OH groups as a result of hydrogen bond. Therefore, both calcium ions and phosphate ionic groups rally around the surfaces and accumulate to such extent that heterogeneous nucleation of apatite occurs.

We claim:

1. A process for the preparation of a coating material for the use on biomedical implants wherein a gel-derived titania-based coating is formed according to a sol-gel method and then treated at an elevated temperature of at least 350° C., such that said coating material induces calcium phosphate formation onto its surface under at least one condition of the group consisting of in vitro conditions and in vivo conditions.

2. A process for the preparation of a coating material for use on biomedical implants wherein a gel-derived titania-based coating is formed according to a galvanic method and then treated at an elevated temperature of at least 350° C., such that said coating material induces calcium phosphate formation onto its surface under at least one condition of the group consisting of in vitro conditions and in vivo conditions.

3. A process according to claim 2 wherein the process is carried out in a hydroxide solution where titanium is used as the positive as well as the negative pole.

4. A process according to claim 1 wherein one or more of the following oxides are added to the process: CaO, $P_2O_5$, $Na_2O$, $SiO_2$, $K_2O$, $Al_2O_3$, MgO or $B_2O_3$.

5. A coating composition for biomedical implants comprising mainly a gel-derived titania-based material that has been treated at elevated temperature wherein said material induces calcium phosphate formation onto its surface under at least one condition of the group consisting of in vitro conditions and in vivo conditions, and wherein said elevated temperature is at least 350° C.

6. A coating composition consisting essentially of a gel-derived titania-based material that has been treated at elevated temperature wherein said material induces calcium phosphate formation onto its surface under at least one condition of the group consisting of in vitro conditions and in vivo conditions further comprising as an additive one or more of the following elements either as ions or oxides: Ca, P, Si, Na, K, B, Mg or Al.

7. An implant for biomedical use comprising a substrate and a bone-bonding coating composition thereon wherein said coating composition consists essentially of a gel-derived titania-based coating material that has been treated at an elevated temperature, wherein said elevated temperature is at least 350° C.

8. An implant according to claim 7 wherein the substrate is a tooth, hip or other joint implant or another biomedical implant substrate.

9. An implant according to claim 7 wherein the substrate is at least one substrate selected from the group consisting of polymeric substrates, metallic substrates, ceramic substrates, carbon substrates and a composite substrate comprising at least two of said substrates.

10. An implant according to claim 9 wherein the substrate is titanium or a titanium alloy.

11. An implant according to claim 7 wherein the coating composition further comprises one or more of the following elements either as ions or as oxides: Ca, P, Si, Na, K, B, Mg or Al.

12. An implant for biomedical use comprising a substrate and a bone-bonding apatite layer thereon wherein the apatite layer has been grown on a gel-derived titania coating in an in vitro solution, wherein said gel-derived titania coating was treated, prior to immersion in said solution, at an elevated temperature of at least 350° C.

13. An implant according to claim 12 wherein the solution is an SBF solution.

14. An implant for biomedical use comprising a substrate and a bone-bonding layer thereon wherein the bone-bonding layer is essentially a mixture of gel-derived titania and apatite, said apatite component having been grown on a gel-derived titania coating in an in vitro solution, wherein said gel-derived titania coating was treated, prior to immersion in said solution, at an elevated temperature of at least 350° C.

15. An implant according to claim 14 wherein the solution is an SBF solution.

16. A process according to claim 2 wherein one or more of the following oxides are added to the process: CaO, $P_2O_5$, $Na_2O$, $SiO_2$, $K_2O$, $Al_2O_3$, MgO or $B_2O_3$.

* * * * *